United States Patent [19]

Niskin

[11] Patent Number: 4,593,570

[45] Date of Patent: Jun. 10, 1986

[54] WATER SAMPLER DEVICE WITH KEY

[76] Inventor: Shale J. Niskin, 3415 Chase Ave., Miami Beach, Fla. 33140

[21] Appl. No.: 718,552

[22] Filed: Apr. 1, 1985

[51] Int. Cl.[4] ............................................... G01N 1/10
[52] U.S. Cl. .................................... 73/864.67; 403/383
[58] Field of Search ................. 73/864.67; 403/57, 90, 403/383

[56] References Cited

U.S. PATENT DOCUMENTS

| | | | |
|---|---|---|---|
| 1,111,865 | 9/1914 | Serrell | 403/57 X |
| 4,037,477 | 7/1977 | Niskin | 73/864.67 |
| 4,080,079 | 3/1978 | Waara | 403/57 |
| 4,091,676 | 5/1978 | Niskin | 73/864.67 |

Primary Examiner—Jerry W. Myracle
Attorney, Agent, or Firm—William A. Newton

[57] ABSTRACT

A water sample collecting device for obtaining a sample of water at a predetermined depth consisting of a tubular member with ball valves at both ends and elements for maintaining the valves in a closed position when launched, opening the valves after the device is descending in the water to permit flushing of the device until the device has reached the desired depth when the valves are rotated to the closed position at which time the device containing the sample of water is brought to the surface.

3 Claims, 9 Drawing Figures

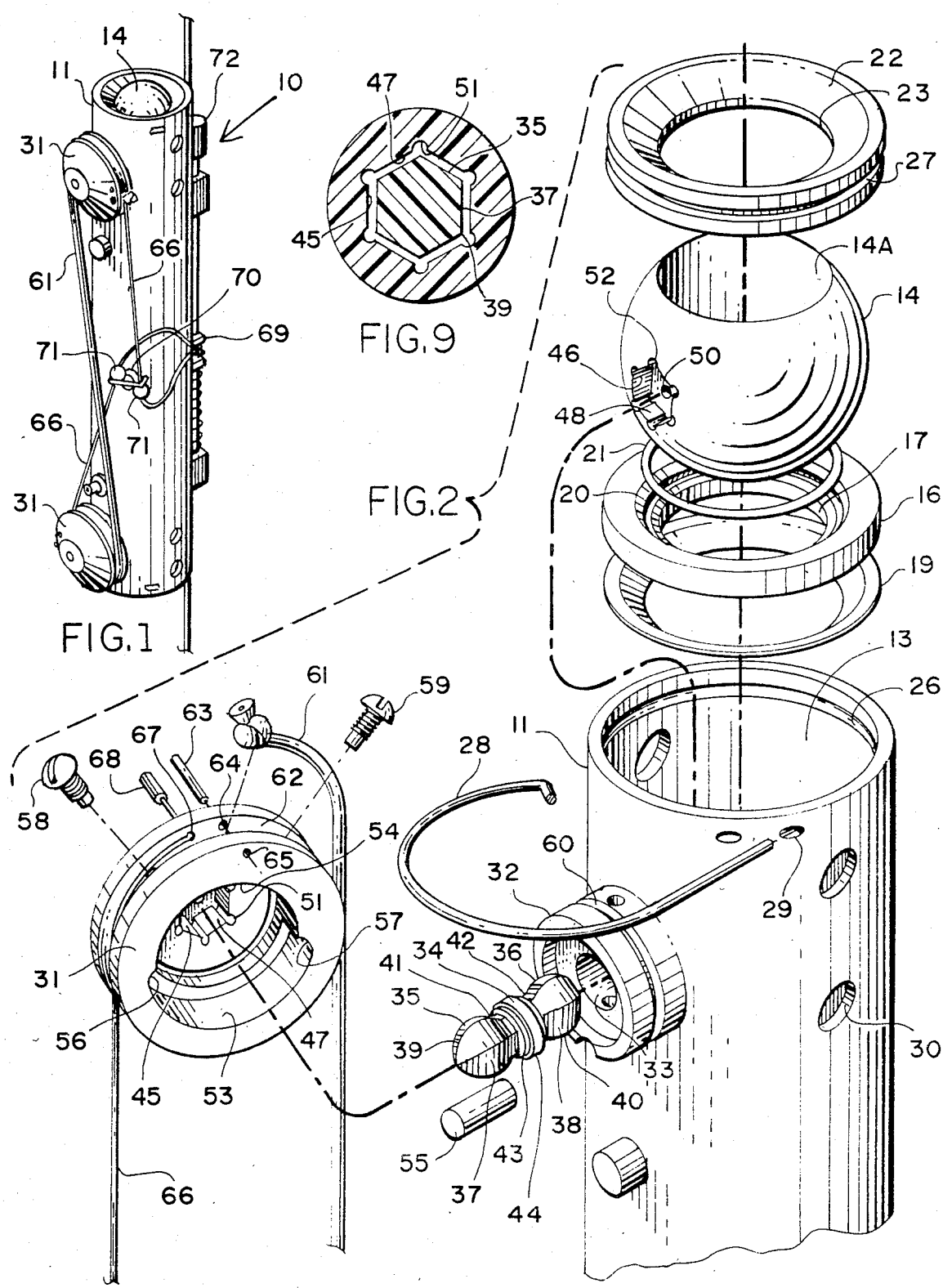

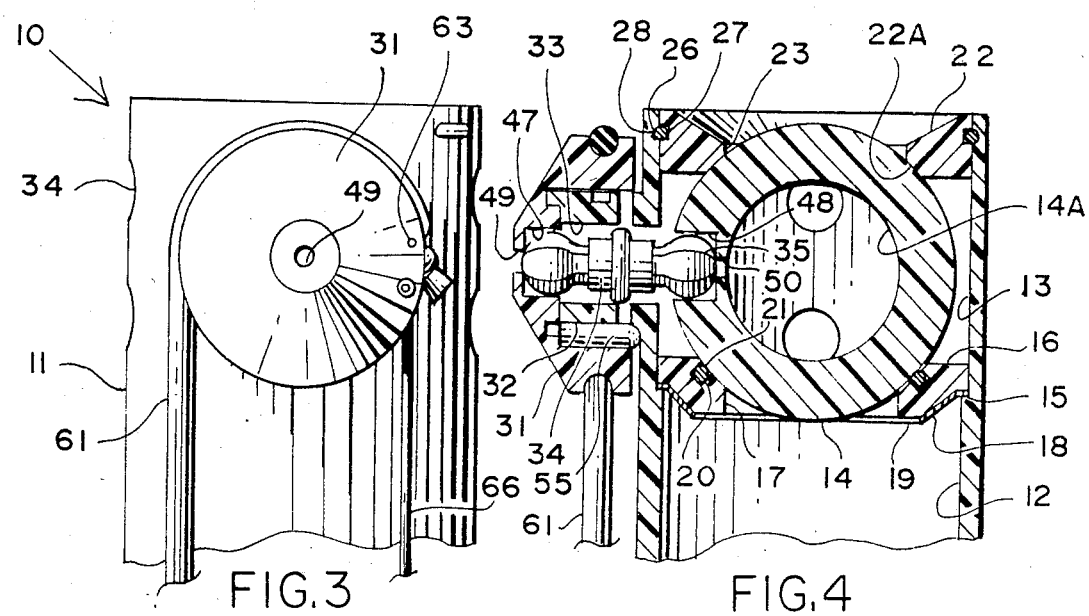
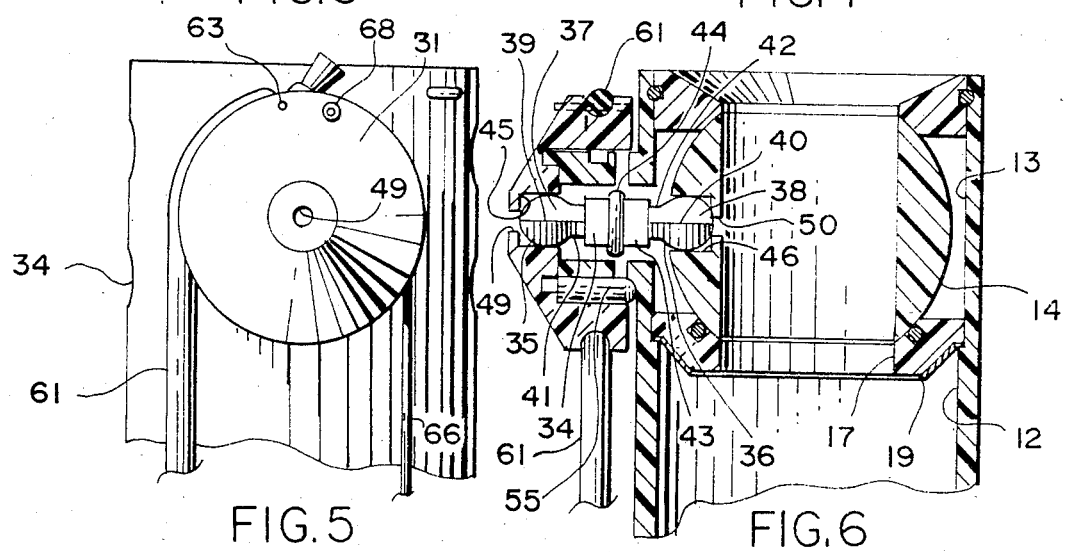
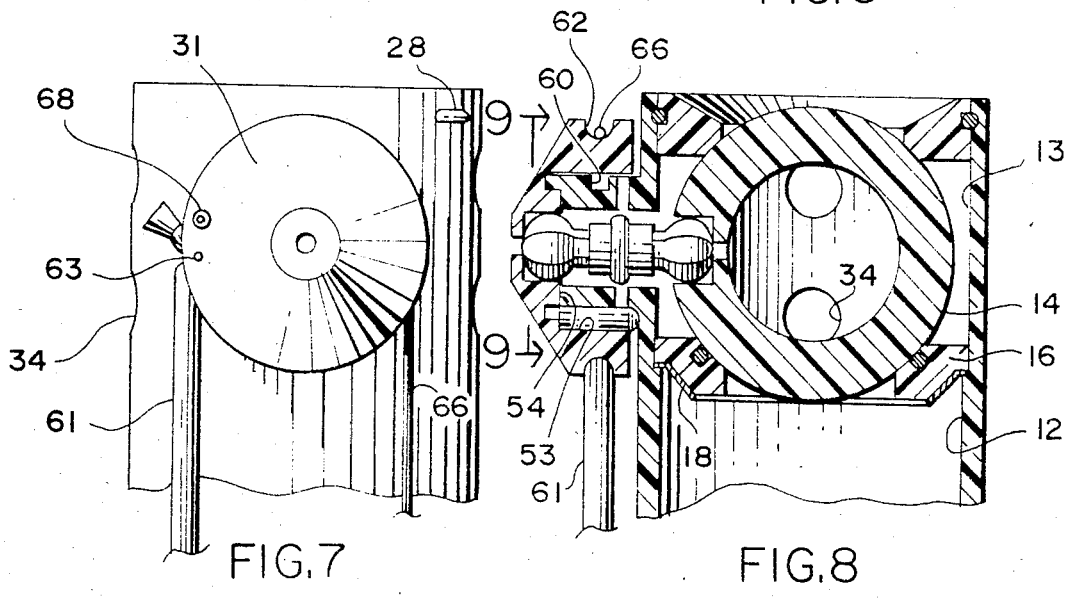

WATER SAMPLER DEVICE WITH KEY

BACKGROUND OF THE INVENTION

1. Field of the Invention

This invention relates to water sample collecting devices.

2. Description of the Prior Art

The present invention is directed toward an improvement in a water sample device shown in U.S. Pat. Nos. 4,091,676 and 4,037,477 to the same inventor as in the subject invention. Referring to FIGS. 14 and 16 in U.S. Pat. No. 4,091,676, a stub shaft extends through a bottle so as to engage a groove on a ball valve so that when a pair of pulleys are rotated the ball valves are rotated from an open position to a closed position and vice-versa. The ball valve was mounted on a free floating valve seat with an outer peripheral shoulder which sealingly engages a peripheral shoulder formed in the interior of the bottle.

The problem with the prior art design described above is that the bottle is formed from standard PVC pipe which is readily available at low cost. This PVC pipe has inner and outer diameters that can vary substantially. As a result, the valve seat can find itself in a variety of offset positions in that it must have an outer diameter dimensioned to accommodate the varying inner diameter of the tubular bottle. Unrestrained, the ball valve will center itself and settle into a good water tight engagement of the valve seats, despite the variations in the diameter of the bottle. However, the stub shaft greatly restrains the movement of the ball valve. For example, when the shaft is fully extended into the groove, movement is prevented in a direction toward the shaft and in a direction toward the walls of the groove. As a result of this restrained freedom of movement of the ball valve, sometimes an imperfect off-center positioning of the ball valve results in water leaks between the ball valve and the valve seat. The present invention is directed toward overcoming this problem.

SUMMARY OF THE INVENTION

In a water sample collecting device having a tubular member with open end tube portions; valve means mounted at the tube end portions; the valve means comprising an outer valve seat having a substantially centrally disposed opening; an inner valve seat having a substantially centrally disposed opening, and a ball valve seated between the valve seats and having a substantially centrally disposed opening; the inner valve seat being responsive to the pressure of the water of the water sample collected at a predetermined depth and slidably positioned in the tubular member; and the outer valve means being mounted at the outer end of the tube end portions, pulley means capable of rotation by predetermined angular amounts, coupling means for coupling the pulley means to the ball valve so that rotation of the pulley means rotates the ball valve so that the openings of the valve seats and the ball valve are aligned to collect the water sample and subsequently non-aligned to contain the water sample, the improvement comprising the coupling means includes a key having a pair of opposed key end portions; the end portions having a plurality of key sides with each key side configured in the shape of a segment of a cylinder and with adjacent key sides coming together to define a plurality of curvilinear edges; the coupling means includes a pair of cavities formed in the ball valve and the pulley means configured and dimensioned to receive the pair of opposed end portions; and the cavities having a plurality of cavity walls with each cavity wall being joined to another by a groove, whereby the ball valve can freely move to provide a water tight seal.

The present invention overcomes the previously described problem of the prior art design by allowing more freedom of movement of the ball valve so that it can consistently form a water tight seal with the inner valve seat.

BRIEF DESCRIPTION OF THE DRAWINGS

Further objects and advantages of the present invention will become apparent as the following description proceeds, taken in conjunction with the accompanying drawings in which:

FIG. 1 is a perspective view of the water sampling device of the present invention.

FIG. 2 is an exploded view of the water sampling device.

FIGS. 3 and 4 show the water sampling device in its initial closed position.

FIGS. 5 and 6 show the water sampling device in its open position either for flushing or obtaining a water sample.

FIGS. 7 and 8 show the water sampling device in its closed position after the water sample is taken and contained therein.

FIG. 9 shows a cross-sectional view of the pulley, the cavity therein and the end portion of the key positioned in the cavity.

DESCRIPTION OF THE PREFERRED EMBODIMENT

Referring to the drawings wherein like numerals are used to designate similar parts throughout the several views, the numeral 10 refers to my water sample collecting device that is identical in operation to the water sampler of my U.S. Pat. No. 4,037,477 and U.S. Pat. No. 4,091,676 but different in the construction of the structure required for rotating the ball valves so as to not restrain their movement in a manner that prevents a water-tight seal. As shown in FIGURES, the water sampler 10 consists of an elongated tubular member or bottle 11 having a chamber 12 at the ends of which are valve chambers (open end tube portions) 13. Within the valve chambers 13 are identical ball valves 14 rotatably mounted therein and having aperatures 14A. Each of the valve chambers 13 is provided with a peripheral shoulder 15 on which an inner ring-shaped valve seat 16 is mounted. The valve seat 16 that has a centrally disposed opening 17 for the flow of water therethrough is provided with an outer peripheral surface 18 which bears on a liner 19 positioned between the surfaces 15 and 18 for sealing the juncture of the outer periphery of the valve seat 16 and inner surface of the bottle 11. An inner peripheral groove 20 extends about the opening 17 receives an O-ring 21 for sealing the valve seat 16 and ball valve 14 against the leakage of water therealong.

A fixed ring-shaped valve seat 22 is mounted at the free ends of the tubular member 11 engaging the ball valves 14 to maintain the ball valves 14 in a firm but rotatable condition within the chambers 13. The outer valve seats 22 are each provided with a centrally disposed opening 23. The outer valve seat 22 is secured to the bottle 11 by peripheral matching grooves 26 and 27 formed on the inner surface of the bottle 11 and outer surface of the outer valve seat 22 respectively and a pliable locking rod 28 received therein, as shown and described in detail in my U.S. Pat. No. 3,986,635, for Closure Locking and Orienting Device. A bore 29 formed in the wall of the bottle 11 in alignment with the grooves 26 and 27 permits the threading of a pliable rod 28 into position in the matching grooves 26 and 27 to secure the valve seat 22. Openings 30 formed in the side walls of the bottle 11 prevent water from being trapped in the valve chamber 13 when the valves 14 are in an open position.

After the bottle 11 is filled with water at the desired depth in the ocean, and the bottle 11 is being pulled upwardly with the valves 14 in a closed position, the higher pressure of the contained water will cause the valve seat 16 and ball valve 14 to slide outwardly, the valve seat 16 to bear more tightly against the ball valve 14, and the ball valve 14 to bear more tightly against the inner surface 22A of the valve set 22.

The ball valves 14 are actuated by pulleys 31 that are each mounted on a collar 32 extending from the bottle 11. The collar has an opening 33. As described to this point, the water sampler device 10 is the same as shown in U.S. Pat. No. 4,091,676 which is incorporated herein.

The improvement of the present invention comprises using a specially configured and designed key 34. The key 34 has a pair of identical bulb-shaped key end portions 35 and 36, with each end portion 35 and 36 having a hexagonal cross-sectional configuration and six curved surfaces 37 and 38 respectively. Each curved surface 37 and 38 has the configuration of a wedge-shaped segment or slice of a cylinder. The six surfaces of both end portions 35 and 36 meet to define six curvilinear edges 39 and 40 respectively, which meet at the outer periphery of the end portions 35 and 36 respectively and extend backward to a pair of neck portions 41 and 42 respectively. The two neck portions 41 and 42 are coupled by a center portion 43 having an optional ring portion 44.

Identical cavities 45 and 46 are formed in the pulleys 31 and the ball valves 14 for receiving the key end portions 35 and 36 respectively. Each of the cavities 45 and 46 have dimensions conforming to the shape and dimensions of the end portions 35 and 36. More specifically, the cavities 45 and 46 each have six flat walls 47 and 48 respectively, configured in the shape of a rectangle that receives the surfaces of the end portions 35 and 36 and which end at walls having optional apertures 49 and 50, respectively. Each of the two sets of flat surfaces 47 and 48 meet at grooves 51 and 52 respectively which are arranged to be adjacent to the curved edges 39 and 40 of the end portions when inserted. The cavities are dimensioned so that the key end portions can slip therein and be removed therefrom during disassembly. Likewise, the cavities 45 and 46 have a hexagonal cross-section configuration. The grooves 51 and 52 are required to allow the end portions 35 and 36 to freely move therein.

The pulleys 31 have an internal cutout that defines a slot 53 which extends approximately 180 degrees about an aperature 54 which has at one end the cavity 47. A pin 55 is secured in a fixed disposition to collar 32 so that it extends inward into the slot 53. The two ends 56 and 57 of the slot 53 form stops that prevent the pulley 31 from rotating in opposite directions after undergoing a predetermined amount of rotation. A pair of screws 58 and 59 extend radially through openings in the pulley 31 so as to protrude into a groove 60 formed in the collar 32, thereby securing the pulley 31 to the collar 32. An elastic member 61 is secured in an outer groove 62 formed in pulley 31 by a pin 63 positioned in holes 64 and 65. A lanyard 66 is secured in the groove 62 by running the same through a hole 67 and attaching an enlarged member 68 to its end. The construction and operation of the lower valve mechanism (pulley 31, valve 14, etc.) is identical to the upper valve mechanism.

The present invention allows the valve ball 14 to float freely with the valve seat 16. This is due to the configuration of the key 34 and the receiving cavities 45 and 46.

The remainder of the structure is the same as shown in U.S. Pat. No. 4,091,676, which is incorporated by specific reference thereto and will only be discussed to the extent required to describe the environment of the invention. The previously described structure of the pin 55 and slot 53 permits the rotation of the pulleys 31 and simultaneous rotation of the valves 14 from an initial closed position as shown by FIGS. 3 and 4 through an arc of 90 degrees to an open position as shown by FIGS. 5 and 6 and then a continued rotation of a further 90 degree arc of the valves 14 to a closed position as shown by FIGS. 7 and 8 so as to collect a water sample. The release mechanisms 69 and 70 that releases the lanyard 66 to allow the above described rotation of the pulleys 31 in FIG. 1 are described in detail in U.S. Pat. No. 4,091,676 and are not part of the present invention. In operation the valves 14 are in a closed position at launching; they rotate 90 degrees to an open position after being launched when the water pressure causes a valve of the release mechanism 70 to be actuated, releasing the balls 71 on the lanyards 66. The lanyards become tightened on the mechanism 69 to permit only a 90 degree rotation of the valves 14 to the open position. Upon the sampler 10 arriving at its desired depth and a messenger striking a slide rod head 72, the lanyards are released and the elastic member 61 forces the continued rotation of the pulleys 31 and the valves 14 to the closed position as shown in FIGS. 7 and 8.

Although particular embodiments of the invention have been shown and described here, there is no intention to thereby limit the invention to the details of such embodiments. On the contrary, the intention is to cover all modifications, alternatives, embodiments, usages and equivalents of the subject invention as fall within the spirit and scope of the invention, specification and the appended claims.

What is claimed is:

1. In a water sample collecting device for collecting a water sample having a tubular member with a pair of open end tube portions; valve means mounted at said open end tube portions; said valve means comprising an outer valve seat having a substantially centrally disposed opening, an inner valve seat having a substantially centrally disposed opening, and a ball valve seated between said valve seats and having a substantially centrally disposed opening; said inner valve seats being responsive to the pressure of the water sample collected at a predetermined depth and being slidably positioned in said tubular member; said outer valve seats being mounted at the outer ends of said open end tube portions, a pair of pulley means capable of rotation by predetermined angular amounts, a pair of coupling means for coupling said pulley means to each said ball valve so that rotation of said pulley means rotates said ball valve whereby said openings of said valve seats and said ball valve are in aligned disposition to collect the water sample and subsequently are in non-aligned disposition to contain the water sample, the improvement comprising:

each said coupling means includes a key having a pair of opposed key end portions;

said key end portions having a plurality of key sides with each said key side configured in the shape of a segment of a cylinder and with adjacent said key sides coming together to define a plurality of curvilinear edges;

each said coupling means includes a pair of cavities formed in said ball valve and said pulley means with each said cavity configured and dimensioned to receive one of said pair of opposed key end portions;

each of said pair of cavities having a plurality of cavity walls; and each of said cavities having a plurality of grooves defined therein, wherein one of said plurality of grooves is formed at each intersection of adjacent said cavity walls, whereby said key end portions can freely move within each of said pair of cavities, whereby said ball valve can freely move to provide a water tight seal.

2. The water sample collecting device of claim 1, wherein said cavity walls are flat.

3. The water sample collecting device of claim 2, wherein each of said pair of cavities has six said cavity walls defining a hexagonal cross section and each of said pair of said key end portions has six said key surfaces defining a hexagonal cross section.

* * * * *